United States Patent [19]

Kötzsch et al.

[11] 4,228,092
[45] Oct. 14, 1980

[54] PROCESS FOR THE PREPARATION OF ORGANOALKOXYSILANES

[75] Inventors: Hans-Joachim Kötzsch; Claus-Dietrich Seiler, both of Rheinfelden; Hans-Joachim Vahlensieck, Wehr, all of Fed. Rep. of Germany

[73] Assignee: Dynamit Nobel Aktiengesellschaft, Troisdorf, Fed. Rep. of Germany

[21] Appl. No.: 605

[22] Filed: Jan. 2, 1979

[30] Foreign Application Priority Data

Jan. 2, 1978 [DE] Fed. Rep. of Germany ....... 2800017

[51] Int. Cl.² .......................... C07F 7/04; C07F 7/18
[52] U.S. Cl. .................................. 556/422; 556/446; 556/471
[58] Field of Search ................................ 260/448.8 R

[56] References Cited

U.S. PATENT DOCUMENTS

| | | | |
|---|---|---|---|
| 3,651,117 | 3/1972 | Bennett et al. | 260/448.8 R |
| 3,792,071 | 2/1974 | Nitzsche et al. | 260/448.8 R |
| 3,985,781 | 10/1976 | Kötzsch et al. | 260/448.8 R |

*Primary Examiner*—Paul F. Shaver

*Attorney, Agent, or Firm*—Sprung, Felfe, Horn, Lynch & Kramer

[57] ABSTRACT

An improvement in a process for the esterification of a organochlorosilane by feeding alcohol into a chlorosilane maintained within a reaction zone without said alcohol contacting said chlorosilane in the gas phase wherein the esterification is performed stepwise with extraction of hydrogen chloride which has developed, the improvement which comprises employing in at least a final esterification step an organochlorosilane of the formula $$H_a R_b SiCl_{4-a-b}$$

wherein
R represents an optionally halogen-substituted alkyl radical which can also contain an oxygen or sulfur atom in the chain, or a halogen or a $NO_2$ group or a protected phenolic group containing aryl radical,
a equals 0, 1, or 2,
b equals 1 or 2, and
a+b amounts to a maximum of 3, said final esterification step being performed with the addition of heat.

8 Claims, No Drawings

PROCESS FOR THE PREPARATION OF ORGANOALKOXYSILANES

BACKGROUND OF THE INVENTION

1. Field of the Invention

This invention relates to a process for the esterification of organo chlorosilanes by contacting the chlorosilanes with alcohol. More especially, this invention relates to a step-by-step esterification of chlorosilanes with alcohols wherein the alcohol contacts the chlorosilane in the liquid phase without contact in the gas phase wherein each step is accompanied by extraction of hydrogen chloride which develops, a final esterification step being carried out endothermically employing an organochlorosilane of the formula $$H_aR_bSiCl_{4-a-b}$$

wherein
- R represents an optionally halo-substituted or O-bridges containing alkyl radical or a halogen or a nitro or a protected phenolic group, containing aryl radical
- a equals 0, 1, or 2,
- b equals 1 or 2, and
- a+b amounts to a maximum of 3.

2. Discussion of the Prior Art

In the esterification of chlorosilanes, a number of difficulties are encountered which influence the purity and yield of the desired esters as well as those products which are produced coincidentally with the preparation of the ester, notably, hydrogen chloride. Heretofore these difficulties have influenced the reaction in a negative way. In addition to the formation of alkyl chlorides and water as essential products from the reaction, hydrogen chloride also forms alkyl ether when the same contacts an alcohol. Together with the alcohols extracted from the gas phase, the organic compounds pollute the recovered hydrogen chloride and render it unsuitable for the preparation of highly pure trichlorosilane, useful in turn in the manufacture of transistors. The reason for this lies in the fact that, since the hydrogen chloride used to form the trichlorosilane is in itself impure, there develops, in addition to the trichlorosilane formed, impurities such as methyldichlorosilane which cannot be properly removed from the trichlorosilane. The presence of impurities such as methyldichlorosilane means that the transistor silicon produced from trichlorosilane is of low grade and unsuitable for use as a transistor.

In addition to the foregoing problems, the water which develops during a side reaction in the esterification of chlorosilanes by alcohols interferes with the esterification reaction itself by way of hydrolysis. This causes the formation of by-products and residues of oligomeric and polymeric organosiloxanes which are of virtually no use owing to their irregular and undefined composition. These by-products represent a considerable loss of material and diminution of yields. In addition, the maneuverability of the esterification reaction to form pure products is encumbered owing to the fact that the polymeric and oligomeric organosiloxanes often exhibit a stubborn retention for silicon chloride values. This interferes with the alcohol dosage and isolation of pure end products.

Another drawback of the prior art procedures becomes evident during esterification of organochlorosilanes with an O-bridges containing alkyl or alkoxy radical. The hydrogen chloride which develops acts ether-separatingly and yields, amongst other things, an undesirable content of organically bound chlorine within the product. The products developed as a result of such process can contain impurities such as compounds possessing a β-chloroethoxy group which may have high toxic properties.

Some of these difficulties can be overcome by esterification of trichlorosilane according to the procedure of German Offenlegungsschrift No. 24 09 731, the disclosure of which is hereby specifically incorporated herein by reference, wherein esterification is carried out at temperatures below 100° C. by feeding alcohol into the trichlorosilane without contacting the trichlorosilane with the alcohol in the gas phase. The hydrogen chloride which develops is removed from the reaction vessel before a final esterification step. The adherence to a reaction temperature below 100° C. is important in accordance with this manipulative technique. For example, when carrying out the complete esterification with methanol at the boiling temperature of the reaction mixture, the reaction mixture which develops contains so many undesirable by-products that effective distillative removal of the trimethoxysilane which forms is impossible.

Transferring the procedure of German Offenlegungsschrift No. 24 09 731 to the esterification of organochlorosilanes presents the difficulty that only a 50 percent yield of the desired ester is realized and such is realized together with impurities of methanol and methyl chloride within the escaping hydrogen chloride.

It is an object of this invention, therefore, to provide a method for the complete esterification of chlorosilanes whereby the above-mentioned side reactions do not occur or occur only to a minor extent in order to achieve high yields of organosilane esters with practically no gaseous by-products in the developing hydrogen chloride.

SUMMARY OF THE INVENTION

In accordance with the foregoing object, a process has now been found for the complete esterification of a organo chlorosilane with an alcohol wherein the alcohol contacts the chlorosilane in the liquid phase without contact in the gas phase, the esterification being carried out step-by-step with extraction of hydrogen chloride which develops at each step. In accordance with the invention, the last esterification step is carried out accompanied by the addition of heat using an organochlorosilane of the formula $$H_aR_bSiCl_{4-a-b}$$

wherein
- R represents an optionally halogen-substituted alkyl radical which can contain an oxygen or sulfur atom in the chain or a halogen or a nitro or protected phenolic group, containing aryl radical,
- a equals 0, 1, or 2,
- b equals 1 or 2, and
- a+b amounts to a maximum of 3.

The last esterification step is preferably carried out at the boiling temperature of the reaction mixture whereby one can, in accordance with the invention, bring the reaction mixture to a boiling temperature only towards the end of the complete esterification.

Compared to known processes which, according to the present state of the art, do not work at increased temperatures, especially at boiling temperature, the inventive process offers surprising advantages in respect of material quantities, control of the reaction parameters and purity of the resultant esters, absence of by-products and waste. The described process provides an almost perfect quantitative yield where the products are free of alcohols, alkyl chlorides and dialkyl ethers. Of particular significance is the fact that the resulting hydrogen chloride is not contaminated by impurities and thus does not provide an environmental problem. More especially, the resultant hydrogen chloride can be used to form trichlorosilane which in turn can be used to form transistor quality silicon.

In accordance with the invention, esters are formed endothermically by reaction of alcohols with organochlorosilanes. The reaction proceeds homogeneously without the occurrence of side reactions, despite the formation of hydrogen chloride according to the reaction's stoichiometry and despite the fact that hydrogen chloride remains present, to some extent, in the reaction mixture before the same is removed therefrom by being boiled off or the like. The hydrogen chloride which ultimately emerges from the reaction mixture does not contain interfering impurities and can be used directly for the chlorination of ferrosilicon and for the preparation of chlorosilanes which, in turn, can be used for the preparation of transistor silicon.

In addition, the inventive process has the advantage that it can be carried out without the use of acid binding agents which are often necessary in known esterification processes. Therefore, the additional preparation steps in this known process, necessary for the separation of the resulting salts, become unnecessary.

The processing principle of the invention, namely the direct feeding of the alcohol component into the admixed chlorosilane without contacting the gas phase of the liquid reaction mixture, is realized in simple technical manner by introducing the alcoholic component in liquid form, accompanied by agitation of the reaction mixture, through a bottom valve or by immersion of the supply conduit.

In this way, one prevents the reaction mixture from entering the supply conduit either by calibration of the supply conduit depending on the amount of material passing through and the rate of admixture or by the use of slightly elevated pressure, corresponding at least to the opposing pressure of the liquid column of the reaction mixture.

The reaction temperatures are not stated in fixed numbers, but appear during the reaction. Starting temperatures may be chosen at random. Normally, they range between +40° C. and +200° C. and, in some instances, correspond to the boiling temperature of the organosilane component. When esterifying several equivalents of chlorine (at a+b=1 or 2), the first reaction steps may be carried out below the boiling temperature, as long as the reaction does not advance to the last equivalent. Corresponding to the endothermic reaction, one should add at least enough heat to prevent the reaction temperature from declining. Before bringing the last esterification equivalent to reaction, the system is to be heated in order to completely extract the hydrogen chloride contained within and finally to complete the esterification with the addition of heat reaching the boiling temperature of the system at the end of the final esterification step. In this reaction step, the addition of heat should at least reach a level whereby the reaction temperature based on the corresponding thermal reaction should not decline. In general, the corresponding reaction temperature of this step ranges between 60° C. and the boiling point of the system. After complete esterification, the developed hydrogen chloride should be extracted again by boiling.

The rate of admixing alcohol and the calibration of the supply conduit can be chosen almost at random within a wide range. It depends essentially on the range and output capacity of the reflux cooler whose function it is to cool deep the escaping hydrogen chloride in order to prevent a carry-over of the synthesized ester.

The pressure regulation of the alcoholic component depends on the counter-pressure of the reaction mixture affecting the intake opening, which counter-pressure must be equalized throughout every phase of the reaction. As additional counter-pressure, 0 to 10 mm water column is deemed sufficient. One can use an even higher pressure. The necessary pressure is achieved in a simple manner by a corresponding elevation of the alcohol supply vessel and in some instances by the use of a regulating valve. Dosing pumps can also be used.

The esterification can also be carried out in the presence of solvents which may be admixed in random concentrations, preferably between 0 percent and 25 percent by volume. Especially, such compounds are used as solvents which reduce the boiling point of the raw product. These are hydrocarbons, such as hexane, heptane, isooctane, benzene, toluol, etc., and hydrocarbon chlorides such as transdichloroethylene, trichloroethylene, perchloroethylene, chlorobenzene, etc.

Organochlorosilanes which can be used in accordance with the present invention have the formula given above. Preferably, R is an alkyl radical of between 1 and 8 carbon atoms which of course may contain a halo-substituent. Additionally, when R is an alkyl radical, the same can contain an oxygen or sulfur atom in the chain. R can also represent an particularly a halogen or a phenolic or a nitro group containing aryl radical. Particularly contemplated organochlorosilanes include methyltrichlorosilane, hydrogenmethyldichlorosilane, hydrogendimethylchlorosilane, dimethyldichlorosilane, trimethylchlorosilane, ethyltrichlorosilane, hydrogenethyldichlorosilane, propyltrichlorosilane, n- and isobutyltrichlorosilane, amyltrichlorosilane, n-octyltrichlorosilane, 2-ethylhexyltrichlorosilane, n-dodecyltrichlorosilane, n-octadecyltrichlorosilane, vinyltrichlorosilane, vinylmethyldichlorosilane, vinyldimethylchlorosilane, allyltrichlorosilane, 2-cyclohexenylethyltrichlorosilane, butenyltrichlorosilane, 3-allyloxypropyltrichlorosilane, benzyltrichlorosilane, benzylmethyldichlorosilane, 2-phenylethyltrichlorosilane, 3-phenoxypropyltrichlorosilane, 3-4'-isopropylphenoxypropyltrichlorosilane, phenyltrichlorosilane, phenylmethyldichlorosilane, diphenyldichlorosilane, chlormethyldimethylchlorosilane, chlormethylmethyldichlorosilane, chlormethyltrichlorosilane, brommethyltrichlorosilane, 2-chlorethyltrichlorosilane, 2-chlorethylmethyldichlorosilane, 3-chlorpropyltrichlorosilane, 3-chlorpropylmethyldichlorosilane, 3-brompropyltrichlorosilane, 3-iodinepropyltrichlorosilane, 3-fluorpropyltrichlorosilane, 3,3,3-trichloropropyltrichlorosilane, 3,3,3-trichloropropylmethyldichlorosilane, 3,3,3-trifluorpropyltrichlorosilane, 4'-isopropylphenoxymethylmethyldichlorosilane, pentabrombenzyltrichlorosilane, 3-pentachlorophenoxypropyltrichlorosilane, 3-2'4'-dichlorophenoxypropyltrichlorosilane, 3-p-nitrophenoxypropyltrichlorosilane and 3-o-methoxyphenoxypropyltrichlorosilane.

The alcoholic starting materials include primary aliphatic alcohols with 1 to 20 C-atoms, such as methanol, n-propanol, the primary butanols, pentanols, hexanols, heptanols, octanols, nonanols, decanols, undecanols, etc., in addition to mono ethers of various glycols, partially known as cellosolve, as for example 2-methoxyethanol, 2-ethoxyethanol, 2-butoxyethanol, diethylglycolmonomethyl ether, diethyleneglycolmonobutyl ether, tetraethyleneglycolmonomethyl ether, etc.

Products which can be prepared advantageously according to the inventive process are those derived from chlorosilanes according to known processes otherwise accessible only in poor yields of methyl ester, for example methyltrimethoxysilane, dimethyldimethoxysilane, hydrogen methyldimethoxysilane, hydrogen dimethylmethoxysilane, propyltrimethoxysilane, isobutyltrimethoxysilane, n-octyltrimethoxysilane, n-octadecyltrimethoxysilane, vinyltrimethoxysilane, vinylmethyldimethoxysilane, phenyltrimethoxysilane, chlormethyldimethylmethoxysilane, chlormethyltrimethoxysilane, 3-chlorpropyltrimethoxysilane, etc., the ethyl esters, as for example, methyltriethoxysilane, dimethyldiethoxysilane, hydrogen methyldiethoxysilane, n-propyltriethoxysilane, amyltriethoxysilane, n-octyltriethoxysilane, n-octadecyltriethoxysilane, vinyltriethoxysilane, vinylmethyldiethoxysilane, vinyldimethylethoxysilane, benzyltriethoxysilane, 4'-isopropylphenoxymethyl(methyl)dimethoxysilane, 3-4'-isopropylphenoxypropyltriethoxysilane, phenyltriethoxysilane, chlormethyldimethylethoxysilane, chlormethyltriethoxysilane, brommethyltriethoxysilane, 2-chlorethyltriethoxysilane, 2-chlorethylmethyldiethoxysilane, 3-chlorpropyltriethoxysilane, 3-brompyltriethoxysilane, 3-iodinepropyltriethoxysilane, 3,3,3-trichlorpropyltriethoxysilane, 3,3,3-trifluoropropyltriethoxysilane, pentabrombenzyltriethoxysilane, etc. Resulting esters with longer alkoxy groups are for example allyltri-n-butoxysilane, vinyltri-2-ethylheoxysilane, vinyl-2-methoxyethoxysilane, chlormethyldimethyl-2-ethoxyethoxysilane, etc.

The resultant products can be used directly in silane ester based anticorrosive coating agents or they can be used as building preservatives or as modifying agents for inorganic oxidic materials. They can also be used for the impregnation of glass including compositions containing glass fibers. Many of the compounds prepared in accordance with the invention, such as the chloroalkyl-containing compounds, are useful as intermediates for the preparation of silanes to be employed as adhesives.

In order to more fully illustrate the nature of the invention and the manner of practicing the same, the following examples are presented:

EXAMPLE 1

Preparation of methyldimethoxysilane from methyldichlorosilane and methanol according to the inventive process:

5.75 kg (50 mol) of methyldichlorosilane are placed into a 10 liter multi-necked vessel with agitator, equipped with a heatable and coolable double sleeve controlled by thermostats, a reflux cooler (0.5 m$^2$) working at $-82°$ C. with a reflux funnel for the condensate and with a discharge conduit for hydrogen chloride, one thermometer each for measuring the temperature of the gas phase and the liquid phase, and a two liter dropping funnel as alcohol supply vessel whose discharge outlet of 2 mm diameter is situated below the liquid surface as immersible tube 2 cm above the bottom of the reaction vessel. The methyldichlorosilane is heated to the boiling point (40° C.).

Within 80 minutes, at a constant rate of 20 g per minute, 1600 g (50 mol) of methanol free of water are admixed through the immersible tube into the constantly boiling mixture, whereby hydrogen chloride starts to escape. Afterwards, after total reflux for 15 minutes, once more, 1600 g (50 mol) of methanol (free of water) are introduced during 15 minutes in the boiling mixture and afterwards the mixture is heated under total reflux for 15 minutes at approximately 62° C. Then, one distills the boiled off raw-product over a column with approximately 20 plates.

The gas chromatographic analysis of the raw-product shows a content of approximately 92 percent methyldimethoxysilane besides approximately 3 percent methylmethoxychlorosilane, approximately 4.7 percent methyltrimethoxysilane, and approximately 0.2 percent methyldimethoxychlorosilane.

The constant gas chromatographic analysis of the evolving hydrogen chloride shows no traces of methylchloride, dimethyl ether or methanol during any phase of the reaction. The portion of evaporated product amounts to 0.1 percent.

After a pre-run containing 89 g methylmethoxychlorosilane, the distillation provides 4.78 kg (approximately 90.2 weight percent) methyldimethoxysilane. The boiling point of the product is around 62° C.; D.$_4^{20}$ = 0.8609. The residual acidity is about 18 ppm of chloride capable of being hydrolyzed.

COMPARATIVE EXAMPLE 1

Esterification of trichlorosilane with methanol analogous to Example 1:

5400 g (40 mol) of trichlorosilane are charged into an apparatus described in Example 1 and heated to the boiling temperature (31.6° C.). Within 80 minutes, 2560 g (80 mol) of methanol free of water are admixed through an immersible tube into the constantly boiling mixture, whereby hydrogen chloride evolves under violent reaction. It is heated for an additional 15 minutes in the reflux condenser and, within 30 minutes, additional methanol (1280 g = 40 mol) is stirred into the constantly boiling mixture, whereby hydrogen chloride evolves again. Afterwards, the reflux condenser is heated for 15 minutes at a temperature of 103° C. and the extracted raw-product is distilled over a 6-plate column for experimental purposes. No pure fraction is obtained, because, after extraction of a small mixing fraction consisting primarily of chlorodimethoxysilane, trimethoxysilane, chlorotrimethoxysilane and tetramethoxysilane without fixed boiling points, the raw-product changes at a temperature of approximately 120° C. in the reflux and during separation of dimethyl ether into an increasingly semi-liquid condensate containing chlorosilane which can not be distilled any further.

The gas chromatographic analysis of the raw-product shows contents of approximately 14 weight percent chloromethoxysilane, 3 weight percent trimethoxysilane, 71 weight percent chlorotrimethoxysilane, and 12 weight percent tetramethoxysilane.

The continuous gas chromatographic analysis of the given off hydrogen chloride shows no content of methyl chloride, dimethyl ether or methanol during any phase of the reaction, but it contains hydrogen. The portion of evaporated product amounts to less than 0.1 weight percent.

COMPARATIVE EXAMPLE 2

Esterification of methyldichlorosilane with methanol without an immersible tube in a reaction step below boiling temperature:

1150 g (10 mol) of methyldichlorosilane are charged into a four liter multi-necked vessel equipped with an interior thermometer reflux cooler (0.2 m$^2$; −82° C.) with a discharge conduit for hydrogen chloride, an ordinary dropping funnel with a conduit extending from the column into the gas phase, an agitator and a double sleeve equipped with thermostats. Within 60 minutes, methanol free of water (640 g=20 mol) is stirred in without heat addition, whereby hydrogen chloride evolves. An interior temperature of 42° C. is attained in the liquid phase. After completion of the methanol addition, the temperature is raised to a boiling point of 96° C. within 30 minutes and the extracted raw-product is subjected to distillation. No pure fraction is obtained but, after extraction of a small mixed fraction consisting primarily of methyldimethoxychlorosilane with no fixed boiling point, the raw-product changes at a boiling temperature of approximately 106° C. under separation of dimethyl ether into an increasingly semi-liquid condensate containing chlorosilane which cannot be distilled any further.

The gas chromatographic analysis of the raw-product shows contents of approximately 6 weight percent methylmethoxychlorosilane and 32 weight percent methyldimethoxychlorosilane besides several higher boiling condensed compounds.

The continuous gas chromatographic analysis of the hydrogen chloride evolving from the reaction points out the presence of considerable amounts of methylchloride, methanol and hydrogen.

COMPARATIVE EXAMPLE 3

Esterification of methyldichlorosilane with methanol without an immersible tube in two reaction steps below boiling temperature:

1150 g (10 mol) methyldichlorosilane are charged into an existing experiment set-up as described in Comparative Example 2. Within 30 minutes, methanol free of water (320 g=10 mol) is stirred in without heat addition, and hydrogen evolves. During the liquid phase the interior temperature stays at 35° C. Within 15 minutes after hydrogen chloride is extracted by heating to the boiling point where it dissolves and, after cooling it down again to 26° C., additional methanol (320 g=10 mol) is added within the following 30 minutes. Hydrogen chloride evolves again, while the interior temperature increases to 38° C. After the methanol addition is completed, the product is heating to the boiling point of 89° C. within 20 minutes, and the extracted raw-product is subjected to distillation.

Just as in Comparative Example 2, no pure fraction is obtained, instead, after extraction of a small mixed fraction consisting predominantly of methyldimethoxychlorosilane without a fixed boiling point and by separating dimethyl ether, the raw-product changes into a condensate which cannot be distilled any further.

COMPARATIVE EXAMPLE 4

Esterification of methyldichlorosilane with methanol by using an immersible tube during two reaction steps below boiling temperature:

Analogous to Example 1, 5750 g (50 mol) of methyldichlorosilane are charged at 19° C. Within 80 minutes, 1600 g (50 mol) of methanol free of water are admixed through the immersible tube whereby hydrogen chloride evolves and the interior temperature declines to +11° C. After the addition is completed, hydrogen chloride dissolved by heating to a boiling point is extracted within 25 minutes. After cooling down to 35° C., an additional 1600 g (50 mol) of methanol is stirred in within 80 minutes and without heat addition. Hydrogen chloride starts to evolve slowly, and the interior temperature increases to 41° C. Afterwards, the product is heated to a boiling point within 40 minutes, whereby the temperature reaches 74° C. in its final stage.

Next to 112 g methyldimethoxychlorosilane and 384 g methyltrimethoxysilane, the distillation provides 672 g methylmethoxychlorosilane and 2594 g methyldimethoxysilane (48 weight percent) as main products. The gas chromatographic analysis of the hydrogen chloride shows contents of approximately 2 weight percent methanol, and traces of methylchloride. The portion of evaporated product amounts to less than 0.04 weight percent.

EXAMPLE 2

Preparation of methyldiethoxysilane from methyldichlorosilane and ethanol according to the inventive process:

Analogous to Example 1, 4600 g (40 mol) of methyldichlorosilane are charged and heated to a boiling point. Within 90 minutes, 1840 g (40 mol) of ethanol free of water are stirred in, and after 20 minutes reflux temperature (approximately 72° C.) an additional 1840 g ethanol are stirred in within 90 minutes. Afterwards, the reflux is boiled for 20 minutes, and the extracted boiling raw-product is drained into the cavity of a six-plate column where it is immediately distilled.

4940 g (92.4 weight percent) of methyldiethoxysilane (Bp. 97° C.; D.4$^{20}$:0.8456) are obtained by distillation after a pre-run containing methylethoxychlorosilane. The distillation residue of 220 g contains primarily methyltriethoxysilane.

The continuous gas chromatographic analysis of the escaping hydrogen chloride shows no traces of ethyl chloride, diethyl ether or ethanol in any phase of the reaction. The portion of evaporated product amounts to less than 0.04 percent by weight.

EXAMPLE 3

Preparation of methyltriethoxysilane from methyltrichlorosilane and ethanol according to the inventive process:

Analogous to Example 1, 4485 g (30 mol) of methyltrichlorosilane are used and heated to near boiling temperature. Over a period of 70 minutes, 1380 g (30 mol) of ethanol free of water are stirred in, whereby hydrogen chloride starts to evolve. Afterwards, the reflux is heated for 20 minutes and an additional 1380 g (30 mol) of ethanol is stirred into the continuously boiling reaction mixture, whereby hydrogen chloride evolves once more. The reflux is heated again for 20 minutes and a third amount of 1380 g (30 mol) ethanol is stirred into the continuously boiling material over a period of 100 minutes. Afterwards, the product is extracted for 30 minutes by heating, and the boiling raw-product is drained into a 6-plate column and is immediately distilled.

The gas chromatographic analysis of the raw material shows a 97 weight percent methyltriethoxysilane content and 1.8 weight percent methyldiethoxychlorosilane as well as 1 weight percent of higher boiling materials.

5110 g (95.7 weight percent) of methyltriethoxysilane (Bp 143° C.; $n_D^{20}$:0.8925) are attained by distillation after a pre-run containing 144 g methyldiethoxychlorosilane.

The continuous gas chromatographic analysis of the escaping hydrogen chloride shows no traces of ethyl chloride, diethyl ether or ethanol within any phase of the reaction. The portion of evaporated product amounts to less than 0.02 weight percent.

COMPARATIVE EXAMPLE 5

Esterification of methyltrichlorosilane with ethanol by using an immersible tube in a reaction step at boiling temperature:

Analogous to Example 3, 4485 g (30 mol) of methyltrichlorosilane are used and during continuous boiling of the sediment, 4140 g (90 mol) of ethanol free of water are stirred in over a period of 240 minutes whereby hydrogen chloride evolves. The raw-product is extracted by boiling for 40 minutes in the reflux, and it is distilled immediately afterwards.

The gas chromatographic analysis of the raw-product shows approximately 11 weight percent methyldiethoxychlorosilane, approximately 68 weight percent methyltriethoxysilane and approximately 20 weight percent higher boiling materials.

504 g methyldiethoxychlorosilane and 3245 g (60.8 weight percent) methyltriethoxysilane are attained by distillation during the distillation, a continuously increasing separation of diethyl ether is noted.

The continuous gas chromatographic analysis of the escaping hydrogen chloride shows traces of ethanol and ethyl chloride. The portion of evaporated product amounts to less than 0.02 weight percent.

EXAMPLE 4

Preparation of isobutyltrimethoxysilane from isobutyltrichlorosilane and methanol:

1147 g (6 kMol) of isobutyltrichlorosilane are charged into an enamelled 2 m³ vessel with agitator, equipped with heatable and coolable double sleeve, a reflux cooler (40 m²) working at −49° C., with reflux funnel for the condensate and a discharge conduit for hydrogen chloride (for re-use), thermometers for measuring in the gas and liquid phase, an alcohol collector of 2000 l volume capacity with regulating valve, equipped with a discharge outlet of 15 mm inner diameter emptying into the reactor 34 cm above the tovispherical bottom of the reactor whose intake conduit shows a declining height of about 4.50 m above the mound of the discharge outlet.

Over a period of 130 minutes and at a starting temperature of 40° C., 384 kg (12 kMol) of methanol (free of water) are stirred in by means of the immersible tube and at a constant rate of approximately 3 kg per minute. In the beginning, the temperatures decline by a few degrees and are maintained between 43° C. and 48° C. by heating. After the addition is completed the product is extracted by heating it to 140° C. and afterwards, under constant heating to slowly rising boiling temperature, an additional amount of 192 kg (6 kMol) methanol free of water is stirred in at a constant rate of 3 kg per minute. The temperature rises to 155° C. The boiling raw product is drained for distillation into the cavity of a 12-plate column containing 25 mm pawl racks.

The gas chromatographic analysis of the raw-product shows amounts of 98.3 weight percent isobutyltrimethoxysilane, approximately 1 weight percent isobutyldimethoxychlorosilane and 0.6 weight percent diisobutyltetramethoxydisiloxane.

The continuous gas chromatographic analysis of the escaping hydrogen chloride shows no traces of methyl chloride or dimethyl ether in any phase of the reaction.

After a pre-run containing approximately 32 kg isobutyldimethoxychlorosilane, the distillation provides 1020 kg (approximately 95.7 weight percent) of isobutyltrimethoxysilane. The boiling point is about 155° C. The residual acidity is about 20 ppm of chloride capable of hydrolysis.

In total, approximately 400 Nm³ of hydrogen chloride has been obtained as by-product. A partial stream of the hydrogen chloride is reacted in known fashion with ferrosilicon at 320° C. in a fluidized bed-reactor and converted to trichlorosilane. Within the trichlorosilane obtained there are no traces of methyldichlorosilane.

The semi-conductor silicon obtained by treatment of the same with hydrogen chloride and epitaxy shows less than 1 ppm carbon.

EXAMPLE 5

Preparation of vinyltriethoxysilane from vinyltrichlorosilane and ethanol:

1292 kg (8 kMol) vinyltrichlorosilane are charged into a vessel similar to that described in Example 4. Over a period of 120 minutes, 736 kg (16 kMol) ethanol (free of water) are stirred in through an immersible tube at a constant rate of approximately 6 kg per minute at a starting temperature of 52° C.

Within a few minutes the temperature of both liquid and gas phase start to decline and are maintained between 50°-60° C. by means of heating. Over a period of 110 minutes the reaction mixture is brought to a boil (145° C.) whereby hydrogen chloride escapes and an additional 368 kg (8 kMol) ethanol (free of water) is stirred into the reaction mixture at a constant rate of approximately 3 kg per minute. The boiling point rises to 164° C. Afterwards, the product is distilled in a manner similar to that of Example 4.

The gas chromatographic analysis of the raw-product shows approximately 97.6 weight percent vinyltriethoxysilane besides approximately 1 weight percent divinyltetraethoxydisiloxane and approximately 1 weight percent vinyldiethoxychlorosilane.

The continuous gas chromatographic analysis of the escaping hydrogen chloride shows no traces of ethyl chloride, ethanol or diethyl ether. The portion of the evaporated product amounts to less than 0.01 weight percent.

After a pre-run of approximately 20 kg vinyldiethoxysilane, the distillation provides 1477 kg (97 weight percent) vinyltriethoxysilane. The boiling point is about 164° C. The residual acidity is about 20 ppm of chloride capable of hydrolysis.

In total, 535 Nm³ hydrogen chloride is obtained as by-product. In the trichlorosilane derived in a manner analogous to Example 4, no methyldichlorosilane can be found. The semi-conductor silicon obtained by treatment of the same with hydrogen chloride and epitaxy shows less than 1 ppm carbon.

EXAMPLE 6

Preparation of vinyltri-2-methoxyethoxysilane from vinyltrichlorosilane and 2-methoxy ethanol:

626 kg (4 kMol) vinyltrichlorosilane is charged into a vessel similar to that described in Example 4, with the addition of a Busch-vacuum pump. With a reaction temperature ranging between 60°–80° C. 304 kg (4 kMol) 2-methoxyethanol is stirred in, followed by extraction of the reaction material for 20 minutes at 80 Torr. Within an additional period of 160 minutes, another 304 kg (4 kMol) 2-methoxyethanol is stirred in and the mixture is extracted again (at 50 Torr). The boiling point of 120° C. is achieved with vacuum-assistance and maintained, while another 304 kg (4 kMol) 2-methoxyethanol is stirred in over an additional period of 160 minutes. Finally, the mixture is heated at 2 Torr and the raw-product is distilled over a column with an expansion metal lining (Kloss column).

The gas chromatographic analysis of the raw-product shows 95.8 weight percent vinyltri-2-methoxyethoxysilane.

The gas chromatographic analysis of the escaping hydrogen chloride does not show any organic admixtures.

After a pre-run of approximately 32 kg vinyldi-2-methoxyethoxychlorosilane, the distillation provides 1037 kg (93.6 weight percent) vinyltri-2-methoxyethoxysilane. The boiling point of the product is around 113° C. (1 Torr); $D_{.4}^{20}$:1.04.

The residual acidity is around 42 ppm of chloride capable of hydrolysis. 212 ppm of total chlorine is found.

EXAMPLE 7

Preparation of 3-4'-isopropylphenoxypropyltrimethoxysilane from 3-4'-isopropylphenoxypropyltrichlorosilane and methanol:

2492 g (8 mol) 3-4'-isopropylphenoxypropyltrichlorosilane is charged together with 400 ml trichloroethylene into a 4-liter multi-necked vessel with agitator, interior thermometer, a double sleeve controlled by thermostats, a reflux cooler working at −80° C. with a reflux funnel for the condensate and a gas discharge conduit and a dripping funnel for an alcohol supply vessel, with a discharge outlet of 1 mm inner diameter, commencing 2 cm above the bottom of the reaction column below the liquid surface, while heated to 60° C.

Over a period of 40 minutes, 512 g (16 mol) of methanol (free of water) is stirred in through an immersible tube at a constant rate of approximately 13 g per minute whereby a temperature of 60°–70° C. is maintained by heat assistance. Afterwards, the product is extracted by boiling in the reflux for 30 minutes, over an additional 20 minute period 256 g (8 mol) ethanol is admixed. Afterwards, the product is again extracted for 20 minutes by boiling in the reflux and is finally worked up by distillation.

The distillation provides 2074 g (87 percent yield) of 3-4'-isopropylphenoxypropyltrimethoxysilane with a boiling point at 124° C. (0.1 Torr); $D_{.4}^{20}$:1.031.

| Elemental Analysis: | C | H | Si |
|---|---|---|---|
| Projected for $C_{15}H_{26}O_4Si$ | 60.4 percent | 8.7 percent | 9.3 percent |
| Actual Result | 60.3 percent | 8.9 percent | 9.2 percent |

EXAMPLE 8

Preparation of chloromethyldimethylethoxysilane from chloromethyldimethylchlorosilane and ethanol:

2680 g (20 mol) chlormethyldimethylchlorosilane is heated to 90° C. and charged into a 6-liter multi-necked reaction vessel with agitator, equipped with a double sleeve controlled by thermostats for heating and cooling, a reflux cooler (0.2 m²) working at −48° C. with a reflux funnel for the condensate and a gas discharge conduit for hydrogen chloride, one thermometer each for measuring in the gas phase and liquid phase with a dropping funnel as alcohol collector, whose discharge outlet of 1 mm inner diameter exits 2 cm above the bottom of the reaction vessel below the liquid surface. Over a period of approximately 60 minutes, 644 g (14 mol) ethanol free of water is admixed through a submersible tube at a constant rate of approximately 10 g per minute, whereby hydrogen chloride evolves. The interior temperature is maintained at 90° C. by means of heat assistance. Over a period of 30 minutes, the sediment is extracted by increasing the interior temperature to approximately 122° C. After 10 minutes of boiling in the reflux an additional 276 g (6 mol) of ethanol free of water is admixed over a period of 30 minutes whereby the reaction mixture is kept simmering by means of constant heat. In the meantime, the interior temperature rises up to 135° C. After an additional 10 minutes at reflux temperature the raw-product is distilled.

The distillation provides 2980 g (97.7 percent yield) of chlormethyldimethylethoxysilane, Bp 134.6° C.; $D_{.4}^{20}$0.951.

EXAMPLE 9

Preparation of 2-chloroethyltriethoxysilane from 2-chloroethyltrichlorosilane and ethanol:

Analogous to Example 4, 1188 kg (6 kMol) of 2-chloroethyltrichlorosilane are charged and mixed with 200 liter trichloroethylene.

Over a period of 150 minutes, 276 kg (6 kMol) of ethanol free of water are admixed at 60° C. Afterwards, the product is heated to 70° C. (boiling point approximately 90° C.) and an additional 276 kg (6 kMol) of ethanol is added in a similar manner. After repeated heating, the reaction mixture is kept simmering and completed by adding once more 276 kg (6 kMol) of ethanol over a period of approximately 120 minutes. Vacuum distillation analogous to Example 6 provides 1302 kg (95.8 percent yield) of 2-chloroethyltriethoxysilane, boiling point 59° C., (1 Torr) $D_{.4}^{20}$:1.012.

EXAMPLE 10

Preparation of 3-chloropropyltrimethoxysilane from 3-chloropropyltrichlorosilane and methanol:

Analogous to Example 4, 1696 kg (8 kMol) of 3-chloropropyltrichlorosilane is esterified in two esterification steps at 50° C. with 512 kg (16 kMol) of ethanol and once more with 256 kg (8 kMol) of methanol by slowly increasing boiling temperature. Upon completion, the above are distilled in a vacuum. The vacuum distillation provides 1513 kg (95.2 percent yield) of 3-chloropropyltrimethoxysilane, boiling point 82° C. (30 Torr) $D_{.4}^{20}$:1.08.

What is claimed is:

1. An improvement in a process for the esterification of an organochlorosilane by feeding alcohol into a chlorosilane maintained within a reaction zone without said alcohol contacting said chlorosilane in the gas phase wherein the esterification is performed stepwise with extraction of hydrogen chloride which has developed, the improvement which comprises employing in at least a final esterification step an organochlorosilane of the formula $H_a R_b Si Cl_{4-a-b}$ wherein
- R represents an optionally halogen-substituted alkyl radical which can also contain an oxygen or sulfur atom in the chain or a halogen or a $NO_2$ group or a protected phenolic group containing aryl radical
- a equals 0, 1, or 2,
- b equals 1 or 2, and
- a+b amounts to a maximum of 3, said final esterification step being performed with the addition of heat, said final esterification step being carried out at the boiling temperature of the reaction mixture.

2. A process according to claim 1 wherein the reaction mixture is maintained at a boiling temperature after sufficient alcohol has been added to esterify the last chlorine atom.

3. A process according to claim 1 wherein the esterification is carried out in the absence of an acid binding agent.

4. A process according to claim 1 wherein R is an alkyl radical of 1 to 8 carbon atoms which can be halogen-substituted or can contain an oxygen or sulfur atoms in the chain.

5. A process according to claim 1 wherein R is an aryl radical containing a halogen or a phenolic or a nitro group.

6. A process according to claim 1 wherein said organochlorosilane is selected from the group consisting of methyltrichlorosilane, hydrogenmethyldichlorosilane, hydrogendimethylchlorosilane, dimethyldichlorosilane, trimethylchlorosilane, ethyltrichlorosilane, hydrogenethyldichlorosilane, propyltrichlorosilane, n- and isobutyltrichlorosilane, amyltrichlorosilane, n-octyltrichlorosilane, 2-ethylhexyltrichlorosilane, n-dodecyltrichlorosilane, n-octadecyltrichlorosilane, vinyltrichlorosilane, vinylmethyldichlorosilane, vinyldimethylchlorosilane, allyltrichlorosilane, 2-cyclohexenylethyltrichlorosilane, butenyltrichlorosilane, 3-allyloxypropyltrichlorosilane, benzyltrichlorosilane, benzylmethyldichlorosilane, 2-phenylethyltrichlorosilane, 3-phenoxypropyltrichlorosilane, 3-4'-isopropylphenoxypropyltrichlorosilane, phenyltrichlorosilane, phenylmethyldichlorosilane, diphenyldichlorosilane, chlormethyldimethylchlorosilane, chlormethylmethyldichlorosilane, chlormethyltrichlorosilane, brommethyltrichlorosilane, 2-chlorethyltrichlorosilane, 2-chlorethylmethyldichlorosilane, 3-chlorpropyltrichlorosilane, 3-chlorpropylmethyldichlorosilane, 3-brompropyltrichlorosilane, 3-iodinepropyltrichlorosilane, 3-fluorpropyltrichlorosilane, 3,3,3-trichloropropyltrichlorosilane, 3,3,3-trichloropropylmethyldichlorosilane, 3,3,3-trifluorpropyltrichlorosilane, 4'-isopropylphenoxymethylmethyldichlorosilane, pentabrombenzyltrichlorosilane, 3-pentachlorophenoxypropyltrichlorosilane, 3-2'4'-dichlorophenoxypropyltrichlorosilane, 3-p-nitrophenoxypropyltrichlorosilane and 3-o-methoxyphenoxypropyltrichlorosilane.

7. A process according to claim 1 wherein said alcohol is an aliphatic alcohol having 1 to 20 carbon atoms.

8. A process according to claim 7 wherein said alcohol is selected from the group consisting of methanol, n-propanol, a butanol, a pentanol, a hexanol, a heptanol, an octanol, a nonanol, a decanol, an undecanol, 2-methoxyethanol, 2-ethoxyethanol, 2-butoxyethanol, diethylglycolmonomethyl ether, diethyleneglycolmonobutyl ether and tetraethyleneglycolmonomethyl ether.

* * * * *